United States Patent [19]

Mayer et al.

[11] Patent Number: 5,728,046
[45] Date of Patent: Mar. 17, 1998

[54] SURGICAL RETRACTOR

[75] Inventors: Heinz Michael Mayer, Berlin; Stephan Eckhof, Tuttlingen; Nicola Giordano, Villingen-Schwenningen; Dieter Weisshaupt, Immendingen, all of Germany

[73] Assignee: AESCULAP AG, Tuttlingen, Germany

[21] Appl. No.: 617,339

[22] Filed: Mar. 18, 1996

[30] Foreign Application Priority Data

Jun. 23, 1995 [DE] Germany ............... 195 22 879.0

[51] Int. Cl.$^6$ .............. A61B 11/02; A61B 11/06
[52] U.S. Cl. .............. 600/210; 600/215; 600/217
[58] Field of Search .............. 600/231, 233, 600/215, 216, 210–211, 201, 206, 208, 209, 222, 225, 214, 217; 606/86–88, 90; 269/102, 45

[56] References Cited

U.S. PATENT DOCUMENTS

| | | | |
|---|---|---|---|
| 979,305 | 12/1910 | Hunt | 269/45 |
| 3,522,799 | 8/1970 | Gauthier | 600/233 X |
| 3,749,088 | 7/1973 | Gauthier | 600/215 |
| 4,566,448 | 1/1986 | Rohr | 606/88 |
| 4,805,599 | 2/1989 | Ray | 600/233 |
| 4,867,139 | 9/1989 | Girzadas . | |
| 4,932,395 | 6/1990 | Mehdizadeh | 600/217 |
| 4,971,038 | 11/1990 | Farley . | |
| 5,027,793 | 7/1991 | Engelhardt | 600/210 |
| 5,303,694 | 4/1994 | Mikhail . | |
| 5,363,841 | 11/1994 | Coker . | |
| 5,364,399 | 11/1994 | Lowery | 606/69 |

FOREIGN PATENT DOCUMENTS 0 327 249   8/1989   European Pat. Off. .
2 692 468  12/1993   France .

*Primary Examiner*—Richard J. Apley
*Assistant Examiner*—Denise Pothier
*Attorney, Agent, or Firm*—Barry R. Lipsitz; Ralph F. Hoppin

[57] ABSTRACT

In a surgical retractor having a frame on which at least two retractor elements are mounted, if desired, so as to be displaceable, to enable individual adjustment of the forces exerted by the retractor elements on the surrounding tissue, it is proposed that the frame have at least one support foot which carries attachment means for fixing on a bone.

20 Claims, 3 Drawing Sheets

SURGICAL RETRACTOR

BACKGROUND OF THE INVENTION

The invention relates to a surgical retractor having a frame on which at least two retractor elements are mounted, if desired, so as to be displaceable.

Such retractors are used in surgical operations to reposition muscular tissue, vessels and other parts of tissue with the aid of valves or retractor blades and thereby gain free access to the site of the operation.

It is known to use ring-shaped frames having displaceably mounted thereon several retractor blades which are each positioned at parts of tissue to be repositioned. Such a surgical retractor device is floatingly positioned on the body, and the supporting forces of all the retractor blades are, therefore, equal. Individual proportioning of these forces is not possible with known retractors, although this is highly desirable as such, as the repositioned tissue parts react with different sensitivity to pressure.

The object of the invention is to so design a generic surgical retractor that it is possible to individually adjust the forces which are exerted on the individual parts of tissue repositioned by the retractor.

SUMMARY OF THE INVENTION

This object is accomplished in accordance with the invention in a surgical retractor of the kind described at the outset by the frame having at least one support foot carrying attachment means for fixing on a bone.

In surgical operations, this support foot is fixed on a bone, for example, on a vertebral body of the spinal column by the attachment means, and the frame is thereby brought into a defined position relative to the patient's skeleton. It is, therefore, possible to position the retractor blades with different pressing forces on the individual tissue parts by appropriate displacement on the frame, as the frame is rigidly connected to the patient's skeleton and is no longer floatingly positioned solely by the forces exerted on the retractor blades.

In principle, this is possible with one support foot, but, in accordance with a preferred embodiment, two support feet with attachment means are provided. In particular, these can be held at such a spacing on the frame that the attachment means of the two support feet are fixed on different vertebral bodies.

It is particularly advantageous for the attachment means to comprise a bone screw.

In particular, the bone screw can carry an extension on which the support foot is held.

Bone screws with extensions which can be screwed into bones, in particular, vertebral bodies, are known as such. There are instruments for altering and, where appropriate, correcting the relative position of two vertebral bodies using such bone screws with extensions which are screwed into vertebral bodies. This altered position of the vertebrae can then be fixed by suitable devices which engage the bone screws and the extensions, and so the vertebral bodies can be fixed in the altered position for a healing period of quite long duration.

Such devices which are known per se and consist of bone screw and extension are employed within the scope of the present invention as part of a surgical retractor and serve as attachment means for the frame of such a retractor.

In particular, provision may be made for the support foot to have a borehole for receiving the extension. The support foot can thus be fixed in a simple way on the spinal column or on any other bone section by being positioned on the extension such that the extension penetrates the borehole of the support foot. If two such support feet are used, the frame is held non-rotatably and non-displaceably relative to the body, at least in a plane perpendicular to the extensions, by this positioning alone.

In addition, provision may be made for the support foot to have a retractor blade or to itself be designed as a retractor blade. The support foot itself thus also acts as a bearing surface for surrounding tissue, but, in addition, tissue parts are repositioned by retractor blades on the frame.

It is expedient for the support foot to have sections connected to one another at an angle and for one section to carry attachment means and for the other section to carry the frame. In particular, this is advantageous when the sections carrying the frame lie in a plane arranged parallel to the frame so that repositioning of the frame is achievable by displacement along these sections.

In general, provision is made for the frame to be held so as to be adjustable on the support foot or feet so the frame can be brought into the desired position relative to the bone holding the frame.

In a preferred embodiment, provision is made for the frame to be a closed structure. It can, for example, be formed by four arms connected perpendicularly to one another.

It is also advantageous for the support foot or feet to protrude vertically from the frame.

The following description of a preferred embodiment serves in conjunction with the drawings to explain the invention in further detail.

DETAILED DESCRIPTION OF THE INVENTION

Figure 1:
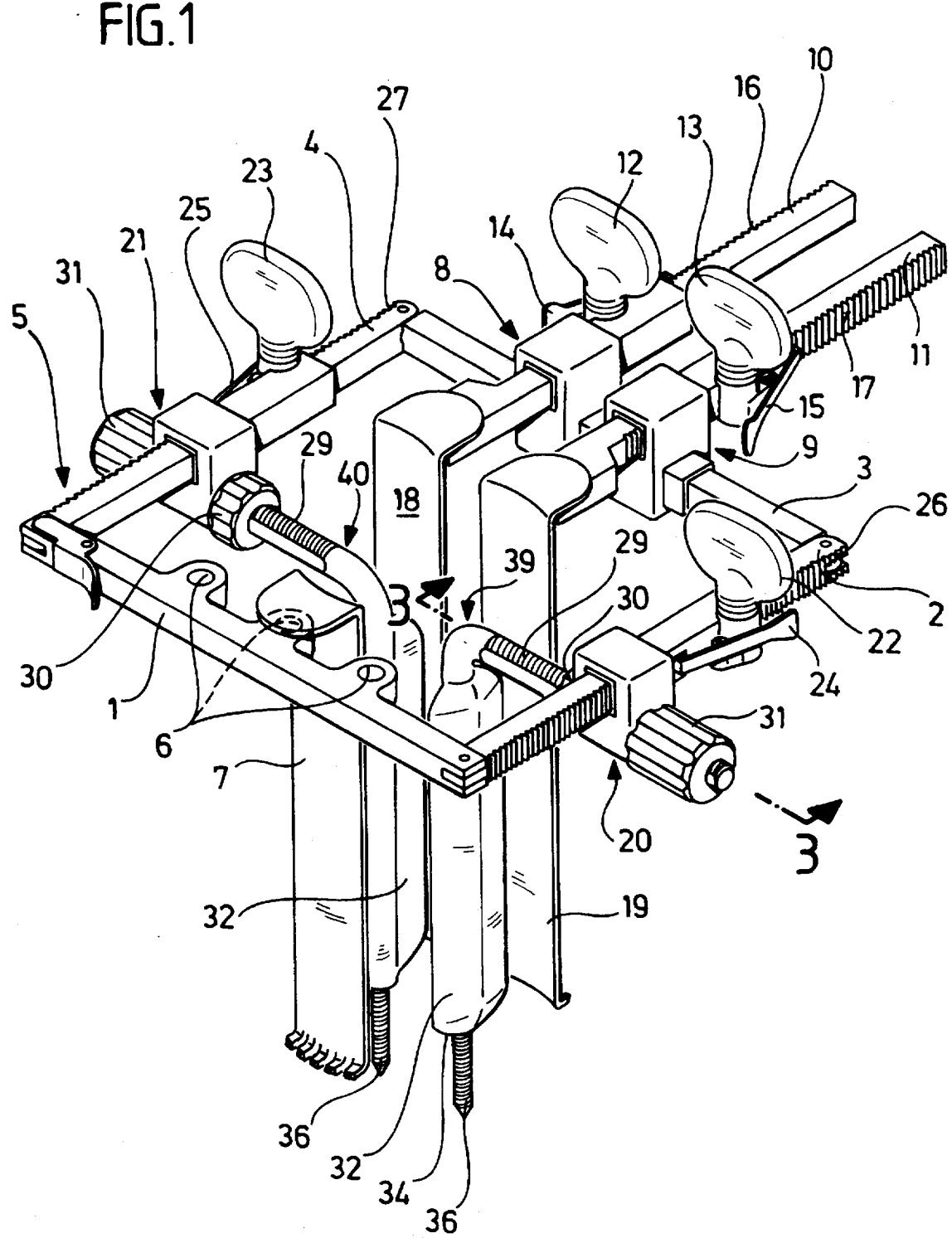
FIG. 1: a perspective view of a surgical retractor with two support feet and three displaceable retractor blades.
Figure 2:
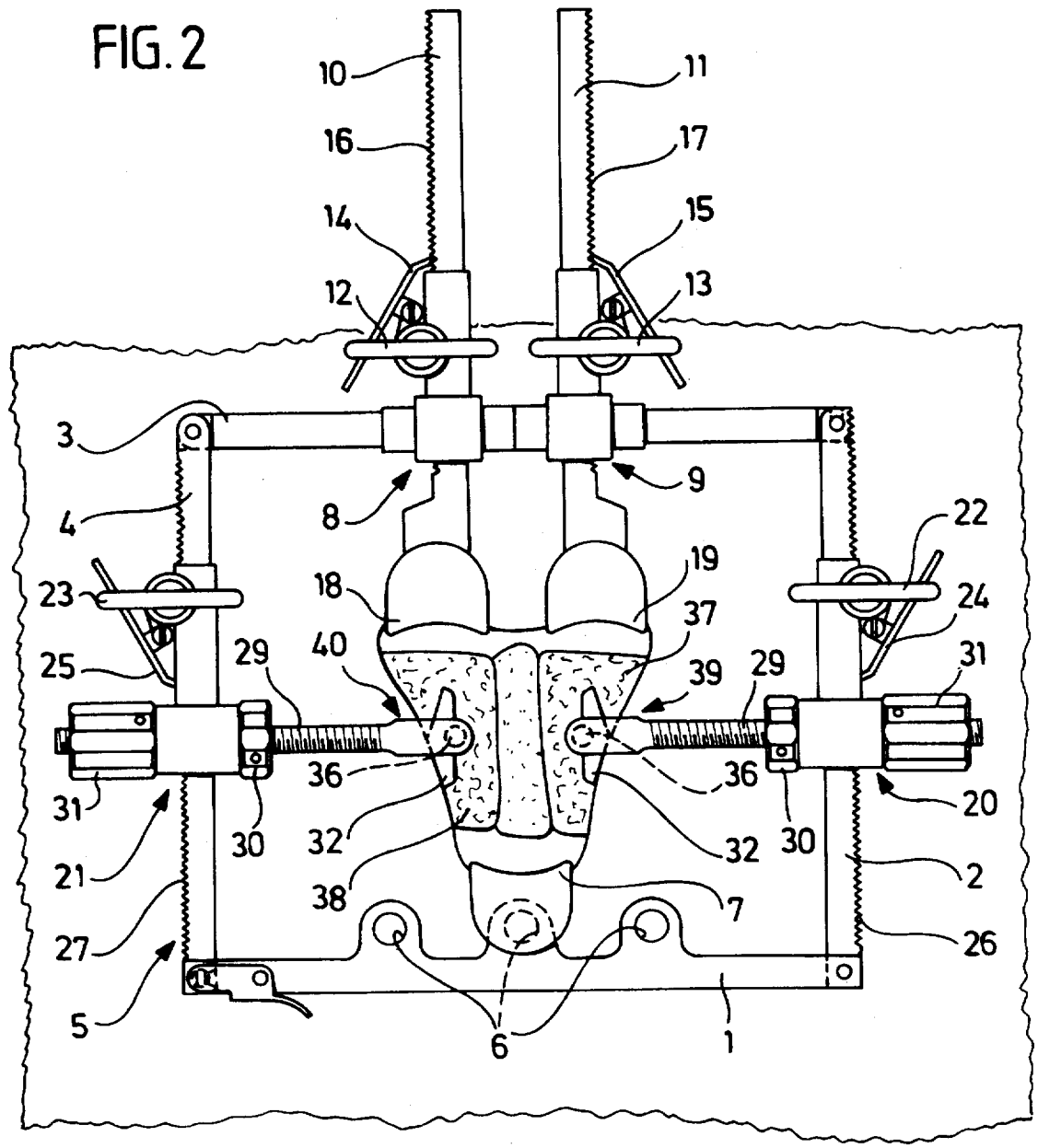
FIG. 2: a plan view of the surgical retractor of FIG. 1 with retractor blades resting on parts of tissue and support feet held on parts of the patient's bone.
Figure 3:
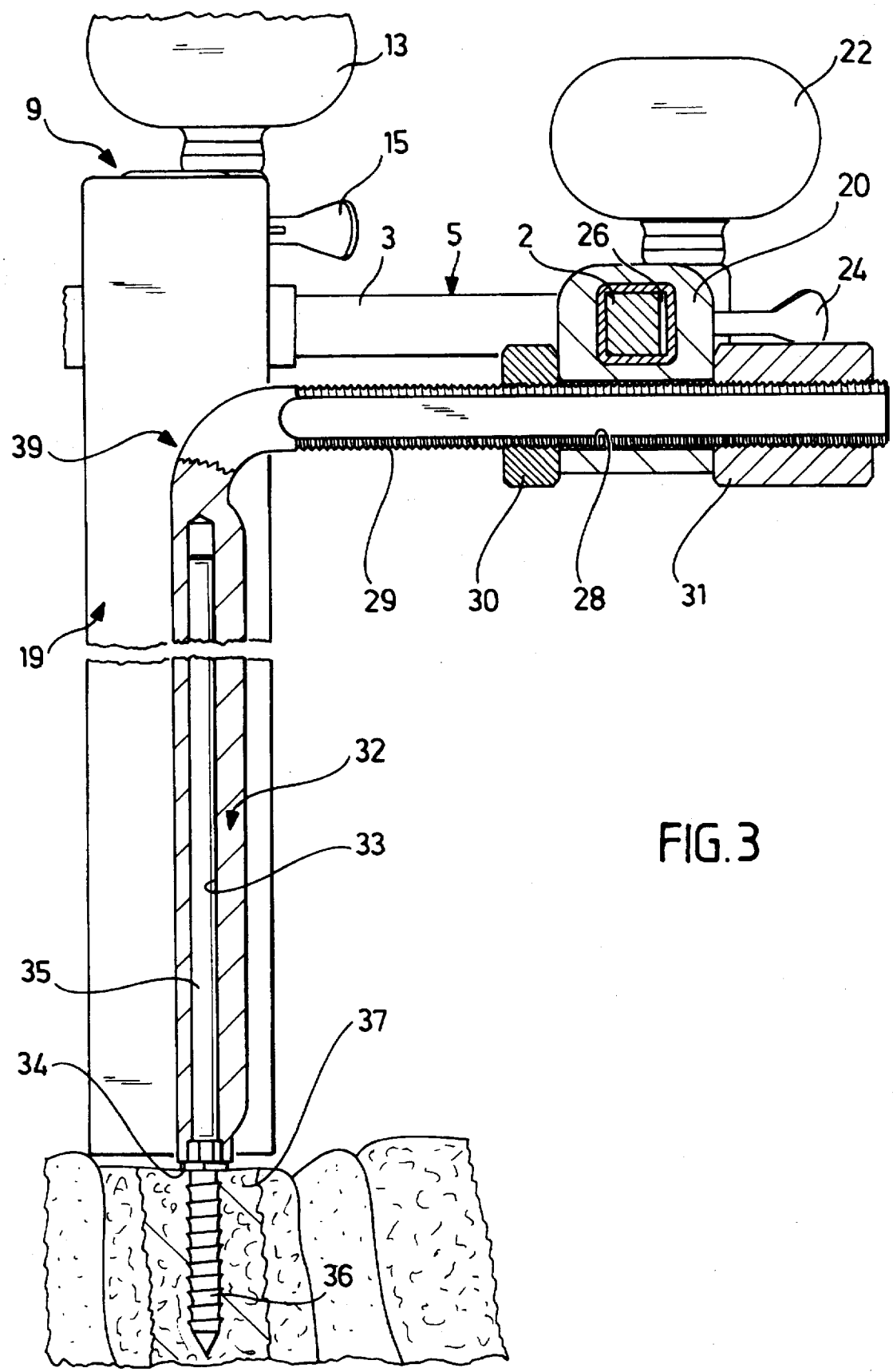
FIG. 3: a sectional view along line 3—3 in FIG. 1.

The retractor illustrated in the drawings comprises four arms 1, 2, 3, 4, which are joined together to form a square frame 5.

Insert eyelets 6 for a retractor blade 7 are arranged on an arm 1. Herein retractor blades are selectively insertable. In the illustrated embodiment, only one such retractor blade 7 is inserted in one of the insert eyelets 6. The retractor blades 7 can be rotatable about the longitudinal axis of the opening of the insert eyelet 6.

On the opposite arm 3, in the illustrated embodiment, two holders 8, 9 are mounted for displacement in the longitudinal direction. These can be fixed in a certain position along the arm 3 by means not visible in the drawings, for example, by a clamping screw.

There is mounted on each holder 8, 9 a holding arm 10 and 11, respectively, in a plane extending parallel to the frame 5 for displacement perpendicularly to the arm 3. The holding arms 10, 11 are clampable by clamping screws 12 and 13, respectively, in the holders 8, 9 so they can only be displaced when the clamping screws 12, 13 are released. In addition, there is associated with each holder 8, 9 a resilient detent device 14 and 15, respectively, engaging in a toothing 16 and 17, respectively, on the holding arms 10 and 11. Therefore, when the clamping screws 12 and 13 are released, the holding arms 10 and 11 are only freely displaceable when the detent devices 14, 15 are also released. This enables rapid fixing while the adjustment is being carried out, and this position is then additionally secured by the clamping screws 12, 13.

Each holding arm 10, 11 carries at its free end a retractor blade 18 and 19, respectively, and, like the retractor blade 7, these protrude vertically from the plane formed by the frame 5.

Mounted for free displacement on each of the two other arms 2, 4 is a holder 20 and 21, respectively, which can be fixed relative to the arms 2 and 4, respectively, by clamping screws 22 and 23, respectively. Also associated with each holder 20, 21 is an elastic detent device 24 and 25, respectively, which cooperates with toothings 26 and 27, respectively, on the arms 2 and 4 so that when the clamping screws 22, 23 are released, the holders 20 and 21 can be pre-fixed in various positions by the detent devices 24 and 25.

Each holder 20, 21 comprises a through-bore 28 which extends transversely to the arms 2 and 4, respectively, and through which a threaded spindle 29 passes. This threaded spindle 29 is fixed in the axial direction by two nuts 30, 31 which are screwed onto it and rest at opposite sides against the holders 20 and 21, respectively. The relative position of the threaded spindle 29 in relation to these holders is adjustable by turning the nuts 30 and 31.

The threaded spindle 29 extending parallel to the plane of the frame 5 and transversely to the arms 2 and 4, respectively, continues into a retractor body 32 which protrudes vertically from the plane of the frame 5. The retractor body 32 is similar in design to a retractor blade but is sufficiently thick to accommodate a blind borehole 33 which extends from its lower end face 34 into the upper region of the retractor body 32.

The blind borehole 33 serves to receive a rod-shaped extension 35 of a bone screw 36. This extension has an external diameter which corresponds to the internal diameter of the blind borehole 33 so the extension 35 can be received substantially free of play in the blind borehole 33.

When inserting the retractor described hereinabove, two bone screws 36 are first screwed with their extensions 35 into the patient's bone, for example, into adjacent vertebral bodies 37, 38 in such a way that the extensions 35 extend parallel to each other.

The retractor described hereinabove is then lowered from above onto the extensions 35 in such a way that the two extensions 35 of the two bone screws 36 dip into corresponding blind boreholes 33 in the two support feet 39, 40 which are each formed by the threaded spindle 29 and the retractor body 32 formed thereon. This is done with the clamping screws 22 and 23 released and also with the threaded spindle 29 being freely displaceable in the holders 20, 21, i.e., before the nuts 30 and 31 are screwed onto the respective holder 20 and 21.

In principle, it is also possible to place the support feet 39 and 40 separately from the frame 5 on the extensions 35 and to only attach the frame 5 to the support feet 39 and 40 subsequently, for example, by mounting the holders 20 and 21.

The frame 5 can be fixed in the desired relative position in relation to the support feet 39 and 40 by the clamping screws 22 and 23 and by the nuts 30 and 31, and so practically a rigid connection of the frame 5 to the vertebral bodies 37 and 38 is achievable.

Finally, the retractor blades 18 and 19 are displaceable to the desired position in relation to the frame 5, and so starting from the frame 5 rigidly connected to the vertebral bodies 37 and 38, the retractor blades are displaceable to the desired positions and rest with the desired force on the tissues to be repositioned.

The device can also be used to alter the spacing between the two support feet 39 and 40 by adjustment of the nuts 30 and 31 and to thereby reposition the vertebral bodies 37 and 38, if this is desired. The retractor thus acquires a double function since it is also useable as a device for repositioning the vertebral bodies.

What is claimed is:

1. A surgical retractor apparatus, comprising:
    a frame defining a central opening adapted to provide access to the site of operation during surgery;
    first and second holders secured to said frame;
    first and second support feet adapted to be secured to said first and second holders respectively and extending into said central opening and away from said frame;
    first and second attachment means for attaching said first and second support feet to respective bone portions; and
    opposing first and second retractor elements secured to said frame, wherein at least said first retractor element is adjustably secured to said frame so as to be displaceable relative to said frame and said second retractor element.

2. The apparatus of claim 1, wherein:
    at least one of said first and second feet is adjustably held by the respective holder so as to be displaceable relative to said frame to provide a displacement of said respective bone portions relative to one another.

3. The apparatus of claim 1, wherein:
    the displacement of said first retractor element is substantially transverse to the displacement of said at least one of said first and second feet.

4. The apparatus of claim 1, wherein:
    said frame extends in a circumferentially closed path to define said central opening.

5. The apparatus of claim 4, wherein:
    said frame is rectangular.

6. The apparatus of claim 1, wherein:
    said bone portions are vertebral bodies.

7. The apparatus of claim 1, wherein:
    said first and second feet are adjustably held by the respective holder so as to be displaceable relative to said frame to allow a displacement of said respective bone portions relative to one another.

8. The apparatus of claim 1, wherein:
    said first and second support feet extend toward one another in said central opening; and
    said first and second support feet extend away from said frame while being substantially parallel to one another.

9. The apparatus of claim 1, wherein:
    said first and second attachment means comprise respective first and second bone screws.

10. The apparatus of claim 9, wherein:
    said first and second bone screws are rigidly coupled to respective first and second extension rods which extend away from said bone portions when said bone screws are secured to said bone portions.

11. The apparatus of claim 10, wherein:
    said first and second support feet are adapted to be supported by said first and second extension rods, respectively.

12. The apparatus of claim 11, wherein:

said first and second support feet have respective first and second boreholes which are adapted to receive said first and second extension rods, respectively.

13. The apparatus of claim 12, wherein:

said first and second boreholes are adapted to removeably receive said first and second extension rods, respectively.

14. The apparatus of claim 12, wherein:

said first and second boreholes are adapted to removeably receive said first and second extension rods, respectively, after said first and second bone screws have been secured to said respective bone portions.

15. The apparatus of claim 1, wherein:

at least one of said first and second support feet is rigidly coupled to a respective retractor blade.

16. The apparatus of claim 1, wherein:

at least one of said first and second support feet is designed integrally with a respective retractor blade.

17. The apparatus of claim 1, wherein:

said frame extends in a plane; and said first and second support feet extend away from said frame substantially perpendicularly to said plane.

18. The apparatus of claim 1, wherein:

said first and second support feet are L shaped.

19. The apparatus of claim 1, wherein:

said first and second support feet include respective threaded spindles for engaging said first and second holders, respectively.

20. The apparatus of claim 19, wherein:

said respective threaded spindles extend substantially collinearly.

* * * * *